US010390920B2

(12) United States Patent
Dai et al.

(10) Patent No.: US 10,390,920 B2
(45) Date of Patent: Aug. 27, 2019

(54) DEVICE FOR INGUINAL LIGAMENT FIXATION AND SURGERY METHOD THEREOF

(71) Applicants: Zhiyuan Dai, Shanghai (CN); Chenyun Dai, Shanghai (CN)

(72) Inventors: Zhiyuan Dai, Shanghai (CN); Chenyun Dai, Shanghai (CN)

( * ) Notice: Subject to any disclaimer, the term of this patent is extended or adjusted under 35 U.S.C. 154(b) by 334 days.

(21) Appl. No.: 15/208,497

(22) Filed: Jul. 12, 2016

(65) Prior Publication Data

US 2016/0317269 A1     Nov. 3, 2016

(30) Foreign Application Priority Data

Oct. 13, 2015   (CN) .................... 2015 2 0801984 U

(51) Int. Cl.
*A61B 17/00*      (2006.01)
*A61F 2/00*       (2006.01)
*A61B 17/04*      (2006.01)

(52) U.S. Cl.
CPC ........ *A61F 2/0004* (2013.01); *A61B 17/0469* (2013.01); *A61F 2/0063* (2013.01); *A61B 2017/00805* (2013.01)

(58) Field of Classification Search
CPC .................... A61B 2017/00805; A61F 2/0063
See application file for complete search history.

(56) References Cited

U.S. PATENT DOCUMENTS

2004/0249473 A1* 12/2004 Delorme ................ A61B 17/06
623/23.64

* cited by examiner

*Primary Examiner* — Kaylee R Wilson

(57) ABSTRACT

A device for inguinal ligament fixation includes a suspension mesh, wherein the suspension includes: a cervix and anterior vaginal wall sling; wherein a first end of the cervix and anterior vaginal wall sling is connected to a cervix or an anterior vaginal wall; two inguinal ligament suspension arms, wherein a second end of each of the two inguinal ligament suspension arms is connected to a second end of the cervix and anterior vaginal wall sling, and the two inguinal ligament suspension arms are placed in a symmetrical form; and two sacral ligament and posterior vaginal wall suspension arms, wherein a second end of each of the two sacral ligament and posterior vaginal wall suspension arms is connected to the second end of the cervix and anterior vaginal wall sling, and the two sacral ligament and posterior vaginal wall suspension arms are placed in a symmetrical form.

1 Claim, 3 Drawing Sheets

DEVICE FOR INGUINAL LIGAMENT FIXATION AND SURGERY METHOD THEREOF

CROSS REFERENCE OF RELATED APPLICATION

The present invention claims priority under 35 U.S.C. 119(a-d) to CN 201520801984.3, filed Oct. 13, 2015.

BACKGROUND OF THE PRESENT INVENTION

Field of Invention

The present invention relates to a technical field of medical instruments, and more particularly to a device for inguinal ligament fixation and surgery methods thereof.

Description of Related Arts

Pelvic organ prolapse, POP for short, mainly refers to pathological decline of uterus, vagina and (or) adjacent organs caused by pelvic tissue degeneration, trauma, congenital dysplasia or postpartum factors of pelvic organs, bladder, uterus, vagina and rectum. POP is a common disease of women, seriously affecting the quality of life of patients. Among women of 50-79 years old, about 40% thereof suffer from varying degrees of pelvic organ prolapse symptoms. Female pelvic floor in the vertical direction is divided into anterior, middle and posterior zone, wherein the middle zone comprises pelvic uterus and vaginal vault. Middle pelvic organ (apex) prolapse (uterine/vaginal vault prolapse) accounts for 20%-30% of pelvic organ prolapse. Due to a "passive" position of uterus during prolapse, single hysterectomy or hysterectomy with vaginal wall repair is insufficient for solving a top-supporting defect, so the recurrence rate, especially vaginal vault prolapse recurrence rate is high. Middle pelvic (apex) prolapse usually happens to relatively young women, and about 72% of middle pelvic (apex) prolapse cases are combined with other pelvic floor dysfunction such as bladder prolapse, rectal prolapse and intestinal hernia. Therefore, middle pelvic organ (apex) prolapse in women is possible to cause urinary tract, anus, rectal and sexual function disorders, leading to serious impact on quality of life, which is one of the thorny clinical issues. Moderate and severe middle pelvic organ (apex) prolapse mainly need surgical treatments. Commonly used clinical surgeries mainly comprise cervical or vaginal mesh sacrocolpopexy, uterosacral ligament fixation and sacrospinous ligament fixation. Purposes of the surgeries are to relieve symptoms, correct deficiencies of pelvic supporting tissues, and maintain or improve organ and sexual functions. In the past 20 years, a lot of scholars have studied fixing points at the middle zone of pelvic cavity (uterine/vaginal vault), wherein the fixing points are mainly located at the uterosacral ligament, sacrospinous ligament and anterior sacral promontory ligament, for fixing the uterus and the vault at these parts, so as to lift the organs. Statistically, surgical treatments of middle pelvic (apex) prolapsed have 30 kinds as estimated, but the fixing points are not in the above areas. However, there are few differences between the above surgical treatments, and risks of recurrence and related complications are high. Abdominal sacrocolpopexy after hysterectomy is one of the surgical treatments for pelvic surgical defects, which bridges a top of the uterus or vagina with sacral anterior longitudinal ligament through a graft, with a long-term success rate of 74% to 98%. However, abdominal sacrocolpopexy after hysterectomy may cause intestinal obstruction, urinary tract infection and haemorrhage due to ruptured anterior sacral veins. In addition, rare nerve damage and sacral osteomyelitis have been reported.

According to all steps of abdominal pelvic floor organ prolapse surgeries, except for uterus lifter used in the patient with uterus remained, vaginal vault and vaginal cuff after hysterectomy needs to be lifted. However, there is no specific device for lifting, and S-shaped or right-angle retractors are used for auxiliary operation, resulting in lack of accuracy and convenience.

SUMMARY OF THE PRESENT INVENTION

An object of the present invention is to provide a device for inguinal ligament fixation and surgery methods thereof for overcoming the above defects, which provides overall repair to a vaginal pelvic cavity and simplifies surgical procedures, wherein the device is reasonable, simple, effective and practical, which further satisfies requirements of overall pelvic repair theories.

Accordingly, in order to accomplish the above object, the present invention provides a device for inguinal ligament fixation, comprising a suspension mesh, wherein suspension mesh comprises:

a cervix and anterior vaginal wall sling (2); wherein a first end of the cervix and anterior vaginal wall sling (2) is fixed on a cervix or an anterior vaginal wall;

two inguinal ligament suspension arms (1), wherein first ends of both the two inguinal ligament suspension arms (1) are respectively fixed on two inguinal ligaments, a second end of each of the two inguinal ligament suspension arms (1) is connected to a second end of the cervix and anterior vaginal wall sling (2), and the two inguinal ligament suspension arms (1) are placed in a symmetrical form; and two sacral ligament and posterior vaginal wall suspension arms (3), wherein a first end of each of the two sacral ligament and posterior vaginal wall suspension arms (3) is fixed on a sacral ligament or a posterior vaginal wall, a second end of each of the two sacral ligament and posterior vaginal wall suspension arms (3) is connected to the second end of the cervix and anterior vaginal wall sling (2), and the two sacral ligament and posterior vaginal wall suspension arms (3) are placed in a symmetrical form.

Preferably, an angle between each of the two sacral ligament and posterior vaginal wall suspension arms (3) and the cervix and anterior vaginal wall sling (2) in length directions is 120 degrees; and an angle between each of the two inguinal ligament suspension arms (1) and the cervix and anterior vaginal wall sling (2) in the length directions is 150-165 degrees.

Preferably, a length of each of the two inguinal ligament suspension arms (1) is 12.0-17.0 cm, and a width thereof is 1.5-2.5 cm; a length of the cervix and anterior vaginal wall sling (2) is 3.5-12.0 cm, and a width thereof is 3.5-4.0 cm; and a length of each of the two sacral ligament and posterior vaginal wall suspension arms (3) is 8.0-12.0 cm, and a width thereof is 1.5-2.5 cm.

Preferably, an angle between each of the two sacral ligament and posterior vaginal wall suspension arms (3) and the cervix and anterior vaginal wall sling (2) in length directions is 180 degrees; and an angle between each of the two inguinal ligament suspension arms (1) and the cervix and anterior vaginal wall sling (2) in the length directions is 90 degrees.

Preferably, a length of each of the two inguinal ligament suspension arms (1) is 12.0-17.0 cm, and a width thereof is 1.5-2.5 cm; a length of the cervix and anterior vaginal wall sling (2) is 3.0-12.0 cm, and a width thereof is 3.0-4.0 cm; and a length of each of the two sacral ligament and posterior vaginal wall suspension arms (3) is 3.0-12.0 cm, and a width thereof is 3.0-4.0 cm.

Preferably, the two inguinal ligament suspension arms (1), the cervix and anterior vaginal wall sling (2), and the two sacral ligament and posterior vaginal wall suspension arms (3) are made of a synthetic material or a biological material.

According to the present invention, the device further comprises a vaginal vault supporting board (4) for supporting and lifting a vaginal vault, wherein the vaginal vault supporting board (4) is 10.0 cm long with two segments, and an angle between the two segments is 150 degrees; the vaginal vault supporting board (4) is 4.0 cm or 5.0 cm wide and 0.3 cm thick.

Preferably, a rear end of the vaginal vault supporting board (4) is connected to a handle which is 25.0 cm long and 1.0 cm wide.

Preferably, the vaginal vault supporting board (4) is made of a heat-resisting repeatable material or a disposable sterile material.

According to the present invention, the device further comprises a vaginal vault cone (5) for supporting and lifting a vaginal vault, wherein the vaginal vault cone (5) is 10.0 cm long with a curved side section and 4.0 cm wide; a front end of the vaginal vault cone (5) is 0.8 cm thick and the vaginal vault cone (5) gradually becomes oval from the front end to a rear end.

Preferably, the rear end of the vaginal vault cone (5) is connected to a handle which is 25.0 cm long and 1.0 cm wide.

Preferably, the vaginal vault vault cone (5) is made of a heat-resisting repeatable material or a disposable sterile material.

A surgery method for inguinal ligament fixation for a patient with uterus remained is provided, comprising steps of: at a bladder lithotomy position of a patient, providing routine disinfection for abdominal and perineal skins, and applying a sterile towel; opening a bladder and back-folding a peritoneum; pushing down the bladder for exposing a vaginal wall; fixing a cervix and anterior vaginal wall sling of a suspension mesh on a cervical isthmus with several absorbable or non-absorbable sutures; respectively suturing two sacral ligament and posterior vaginal wall suspension arms of the suspension mesh on a posterior vaginal wall with the absorbable or non-absorbable suture, and fixing on an inguinal ligament; pulling out two inguinal ligament suspension arms of the suspension mesh along outside portions of peritoneum at two sides of an uterus; opening the peritoneum at a position where a round ligament is attached on the uterus, and suturing the suspension mesh on a myometrium avascular zone under the round ligament with the absorbable or non-absorbable suture; opening the peritoneum below the round ligament; outside the peritoneum and parallel to the round ligament, passing the suspension mesh through anterior superior iliac crest inguinal ligament, fascia and aponeurosis which directly reach an inlet of an inguinal canal, and dragging the suspension mesh until a pre-set length is reached; then opening surface peritoneum of the inguinal ligament and the fascia, and two fixing two inguinal ligament suspension arms on the inguinal ligament, the fascia and the aponeurosis with the absorbable or non-absorbable suture; closing all peritoneal incisions so as to place the suspension mesh outside the peritoneum, and then closing an abdomen.

A surgery method for inguinal ligament fixation for a hysterectomy patient is provided, comprising steps of: providing double-oophorectomy hysterectomy to a patient, and continuously suturing a vaginal cuff with an absorbable suture; lifting the vaginal cuff with a vaginal vault supporting board, lifting with a vaginal vault cone for vaginal vault prolapse patients, and opening a surface membrane of the vaginal cuff; separating a vagina from a bladder with a first gap of 3-4 cm long and 4-5 cm wide, and separating the vagina from a rectum with a second gap of 3-4 cm long and 4-5 cm wide; then fixing with a suspension mesh, wherein specifically, respectively suturing a cervix and anterior vaginal wall sling and two sacral ligament and posterior vaginal wall suspension arms of the suspension mesh on anterior and posterior vaginal wall muscle fibers in different rows with an discontinuous form; opening an inguinal ligament and an aponeurosis surface peritoneum in front of an anterior superior iliac crest outside a round ligament which reach an inlet of an inguinal canal; passing two inguinal ligament suspension arms of the suspension mesh through the anterior superior iliac crest inguinal ligament and fascia which directly reach the inlet of the inguinal canal, and dragging the suspension mesh until a pre-set length is reached; then suturing broken ends of the two inguinal ligament suspension arms on the inguinal ligament and the fascia for 2-3 needles with a non-absorbable suture; suturing the suspension mesh on the round ligament at one position of a peritoneum; suturing an broken end of the round ligament on the vaginal cuff with the absorbable suture; and then closing all peritoneal incisions so as to place the suspension mesh outside the peritoneum.

Therefore, the present invention is able to cure pelvic organ prolapse with one surgery, which provides overall repair to whole pelvic floor and organs and simplifies surgical procedures. The present invention is reasonable, simple, effective and practical, which further satisfies requirements of overall pelvic repair theories. With the present invention, uterus of the patent is able to be remained during surgery, so as to retain physiological and reproductive functions without complications caused by conventional surgeries. For hysterectomy patients, the present invention is sufficient for repairing vaginal vault prolapse and anterior or posterior vaginal wall prolapse, which fully achieves effects of conventional surgical sacrocolpopexy. Especially, the present invention is suitable for treating vaginal vault prolapse of patients who accepted passive hysterectomy due to certain diseases, wherein such patients often suffer from pelvic and intestinal adhesions due to surgeries. However, the present invention will not pass through intestine and ureter, enabling shorter surgical learning curve and less complication risk.

These and other objectives, features, and advantages of the present invention will become apparent from the following detailed description, the accompanying drawings, and the appended claims.

DETAILED DESCRIPTION OF THE PREFERRED EMBODIMENT

Figure 1:
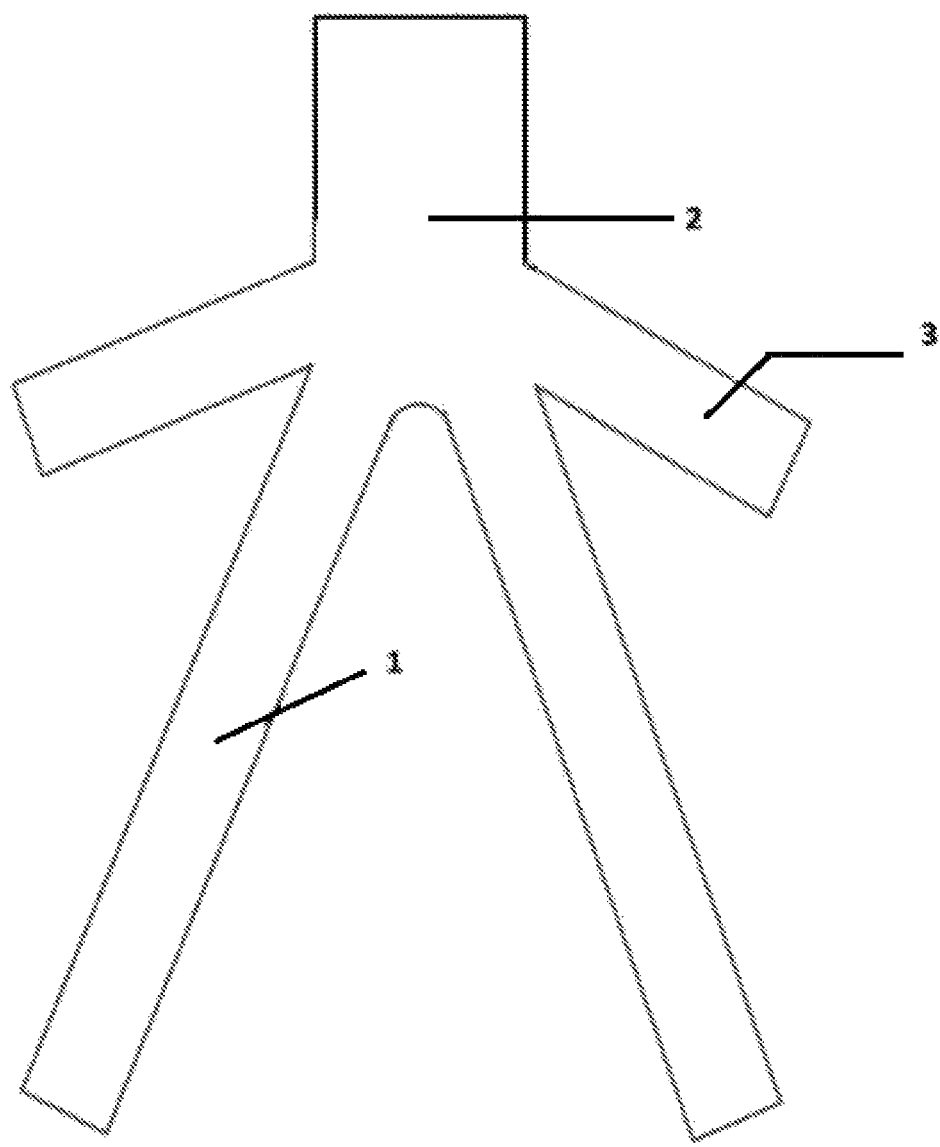
FIG. 1 is a sketch view of a device for inguinal ligament fixation according to a preferred embodiment 1 of the present invention.
Figure 2:
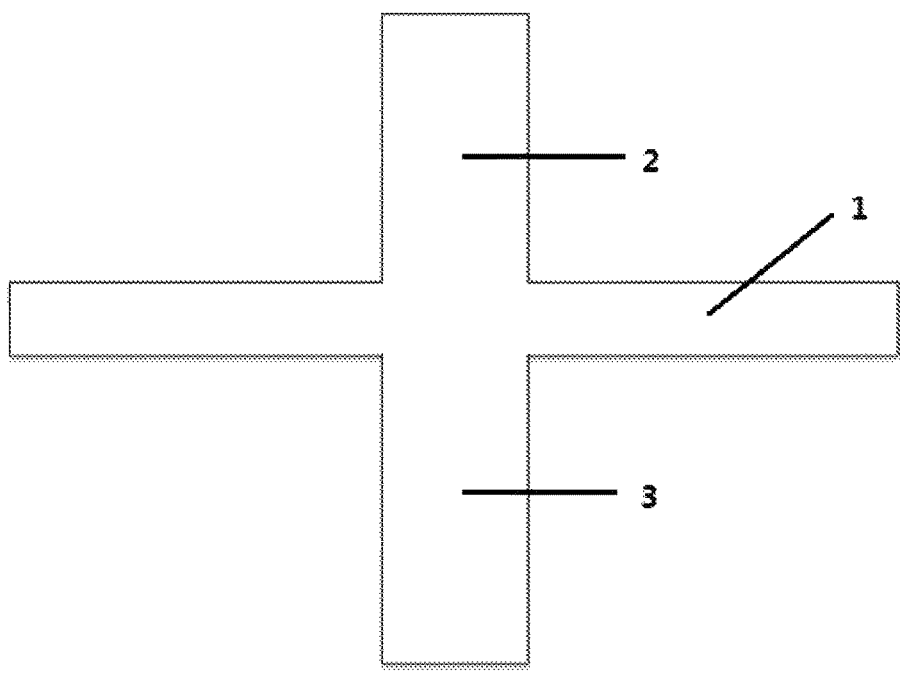
FIG. 2 is a sketch view of the device according to a preferred embodiment 2 of the present invention.
Figure 3:
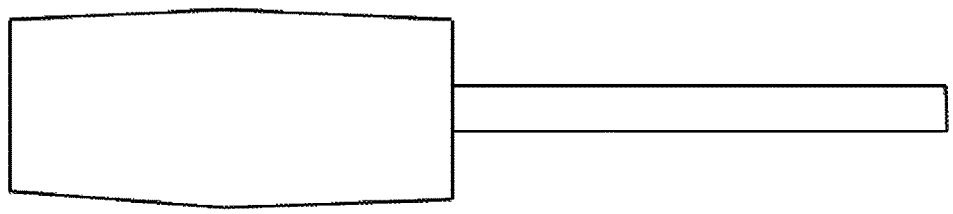
FIG. 3 is a top view of a vaginal vault supporting board according to the preferred embodiment 2 of the present invention.
Figure 4:
FIG. 4 is a side view of the vaginal vault supporting board according to the preferred embodiment 2 of the present invention.
Figure 5:
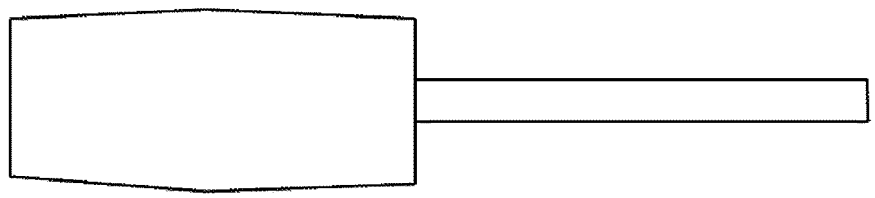
FIG. 5 is a top view of a vaginal vault cone according to the preferred embodiment 2 of the present invention.
Figure 6:
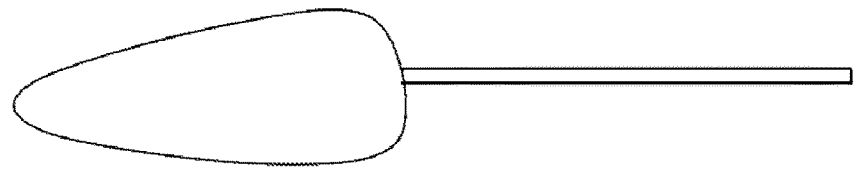
FIG. 6 is a side view of the vaginal vault cone according to the preferred embodiment 2 of the present invention.

Preferred Embodiment 1: Inguinal Ligament Fixation for a Patient With Uterus Remained Referring to FIG. 1 of the drawings, a device for inguinal ligament fixation according to the preferred embodiment 1 of the present invention is illustrated, comprising a suspension mesh, wherein suspension mesh comprises:

a cervix and anterior vaginal wall sling 2; wherein a first end of the cervix and anterior vaginal wall sling 2 is fixed on a cervix;

two inguinal ligament suspension arms 1, wherein first ends of both the two inguinal ligament suspension arms 1 are respectively fixed on two inguinal ligaments, a second end of each of the two inguinal ligament suspension arms 1 is connected to a second end of the cervix and anterior vaginal wall sling 2, and the two inguinal ligament suspension arms 1 are placed in a symmetrical form; and two sacral ligament and posterior vaginal wall suspension arms 3, wherein a first end of each of the two sacral ligament and posterior vaginal wall suspension arms 3 is fixed on a sacral ligament, a second end of each of the two sacral ligament and posterior vaginal wall suspension arms 3 is connected to the second end of the cervix and anterior vaginal wall sling 2, and the two sacral ligament and posterior vaginal wall suspension arms 3 are placed in a symmetrical form.

Preferably, an angle between each of the two sacral ligament and posterior vaginal wall suspension arms 3 and the cervix and anterior vaginal wall sling 2 in length directions is 120 degrees; and an angle between each of the two inguinal ligament suspension arms 1 and the cervix and anterior vaginal wall sling 2 in the length directions is 150-165 degrees.

Preferably, a length of each of the two inguinal ligament suspension arms 1 is 12.0-17.0 cm, and a width thereof is 1.5-2.5 cm; a length of the cervix and anterior vaginal wall sling 2 is 3.5-12.0 cm, and a width thereof is 3.5-4.0 cm; and a length of each of the two sacral ligament and posterior vaginal wall suspension arms 3 is 8.0-12.0 cm, and a width thereof is 1.5-2.5 cm.

Preferably, the two inguinal ligament suspension arms 1, the cervix and anterior vaginal wall sling 2, and the two sacral ligament and posterior vaginal wall suspension arms 3 are made of a synthetic material or a biological material.

A surgery method according to the preferred embodiment 1 comprises steps of: at a bladder lithotomy position of a patient, providing routine disinfection for abdominal and perineal skins, and applying a sterile towel; opening a bladder and back-folding a peritoneum; pushing down the bladder for exposing a vaginal wall; fixing a cervix and anterior vaginal wall sling 2 of a suspension mesh on a cervical isthmus with several absorbable or non-absorbable sutures; respectively suturing two sacral ligament and posterior vaginal wall suspension arms 3 of the suspension mesh on a posterior vaginal wall with the absorbable or non-absorbable suture, and fixing on an inguinal ligament; pulling out two inguinal ligament suspension arms 1 of the suspension mesh along outside portions of peritoneum at two sides of an uterus; opening the peritoneum at a position where a round ligament is attached on the uterus, and suturing the suspension mesh on a myometrium avascular zone under the round ligament with the absorbable or non-absorbable suture; opening the peritoneum below the round ligament; outside the peritoneum and parallel to the round ligament, passing the suspension mesh through anterior superior iliac crest inguinal ligament, fascia and aponeurosis which directly reach an inlet of an inguinal canal, and dragging the suspension mesh until a pre-set length is reached; then opening surface peritoneum of the inguinal ligament and the fascia, and two fixing two inguinal ligament suspension arms 1 on the inguinal ligament, the fascia and the aponeurosis with the absorbable or non-absorbable suture; closing all peritoneal incisions so as to place the suspension mesh outside the peritoneum, and then closing an abdomen. The surgery has been successfully performed in 15 cases.

Preferred Embodiment 2: Inguinal Ligament Fixation for a Hysterectomy Patient

Referring to FIGS. 2-6 of the drawings, a device for inguinal ligament fixation according to the preferred embodiment 1 of the present invention is illustrated, comprising a suspension mesh, wherein suspension mesh comprises:

a cervix and anterior vaginal wall sling 2; wherein a first end of the cervix and anterior vaginal wall sling 2 is fixed on an anterior vaginal wall;

two inguinal ligament suspension arms 1, wherein first ends of both the two inguinal ligament suspension arms 1 are respectively fixed on two inguinal ligaments, a second end of each of the two inguinal ligament suspension arms 1 is connected to a second end of the cervix and anterior vaginal wall sling 2, and the two inguinal ligament suspension arms 1 are placed in a symmetrical form; and two sacral ligament and posterior vaginal wall suspension arms 3, wherein a first end of each of the two sacral ligament and posterior vaginal wall suspension arms 3 is fixed on a posterior vaginal wall, a second end of each of the two sacral ligament and posterior vaginal wall suspension arms 3 is connected to the second end of the cervix and anterior vaginal wall sling 2, and the two sacral ligament and posterior vaginal wall suspension arms 3 are placed in a symmetrical form.

Preferably, an angle between each of the two sacral ligament and posterior vaginal wall suspension arms 3 and the cervix and anterior vaginal wall sling 2 in length directions is 180 degrees; and an angle between each of the two inguinal ligament suspension arms 1 and the cervix and anterior vaginal wall sling 2 in the length directions is 90 degrees.

Preferably, a length of each of the two inguinal ligament suspension arms 1 is 12.0-17.0 cm, and a width thereof is 1.5-2.5 cm; a length of the cervix and anterior vaginal wall sling 2 is 3.0-12.0 cm, and a width thereof is 3.0-4.0 cm; and a length of each of the two sacral ligament and posterior vaginal wall suspension arms 3 is 3.0-12.0 cm, and a width thereof is 3.0-4.0 cm.

Preferably, the two inguinal ligament suspension arms 1, the cervix and anterior vaginal wall sling 2, and the two sacral ligament and posterior vaginal wall suspension arms 3 are made of a synthetic material or a biological material.

According to the preferred embodiment 2, the device further comprises a vaginal vault supporting board 4 for supporting and lifting a vaginal vault, wherein the vaginal vault supporting board 4 is 10.0 cm long with two segments, and an angle between the two segments is 150 degrees; the vaginal vault supporting board 4 is 4.0 cm or 5.0 cm wide and 0.3 cm thick.

Preferably, a rear end of the vaginal vault supporting board 4 is connected to a handle which is 25.0 cm long and 1.0 cm wide.

Preferably, the vaginal vault supporting board 4 is made of a heat-resisting repeatable material or a disposable sterile material.

According to the preferred embodiment 2, the device further comprises a vaginal vault cone 5 for supporting and lifting a vaginal vault, wherein the vaginal vault cone 5 is 10.0 cm long with a curved side section and 4.0 cm wide; a front end of the vaginal vault cone 5 is 0.8 cm thick and the vaginal vault cone 5 gradually becomes oval from the front end to a rear end.

Preferably, the rear end of the vaginal vault cone 5 is connected to a handle which is 25.0 cm long and 1.0 cm wide.

Preferably, the vaginal vault cone 5 is made of a heat-resisting repeatable material or a disposable sterile material.

A surgery method according to the preferred embodiment 2 comprises steps of: providing double-oophorectomy hysterectomy to a patient, and continuously suturing a vaginal cuff with an absorbable suture; lifting the vaginal cuff with a vaginal vault supporting board 4, lifting with a vaginal vault cone 5 for vaginal vault prolapse patients, and opening a surface membrane of the vaginal cuff; separating a vagina from a bladder with a first gap of 3-4 cm long and 4-5 cm wide, and separating the vagina from a rectum with a second gap of 3-4 cm long and 4-5 cm wide; then fixing with a suspension mesh, wherein specifically, respectively suturing a cervix and anterior vaginal wall sling 2 and two sacral ligament and posterior vaginal wall suspension arms 3 of the suspension mesh on anterior and posterior vaginal wall muscle fibers in different rows with an discontinuous form; opening an inguinal ligament and an aponeurosis surface peritoneum in front of an anterior superior iliac crest outside a round ligament which reach an inlet of an inguinal canal; passing two inguinal ligament suspension arms 1 of the suspension mesh through the anterior superior iliac crest inguinal ligament and fascia which directly reach the inlet of the inguinal canal, and dragging the suspension mesh until a pre-set length is reached; then suturing broken ends of the two inguinal ligament suspension arms 1 on the inguinal ligament and the fascia for 2-3 needles with a non-absorbable suture; suturing the suspension mesh on the round ligament at one position of a peritoneum; suturing an broken end of the round ligament on the vaginal cuff with the absorbable suture; and then closing all peritoneal incisions so as to place the suspension mesh outside the peritoneum. The surgery has been successfully performed in 20 cases.

Therefore, the present invention is able to cure pelvic organ prolapse with one surgery, which provides overall repair to whole pelvic floor and simplifies surgical procedures. The present invention is reasonable, simple, effective and practical, which further satisfies requirements of overall pelvic repair theories. With the present invention, uterus of the patent is able to be remained during surgery, so as to retain physiological and reproductive functions without complications caused by conventional surgeries. For hysterectomy patients, the present invention is sufficient for repairing vaginal vault prolapse and anterior or posterior vaginal wall prolapse, which fully achieves effects of conventional surgical sacrocolpopexy. Especially, the present invention is suitable for treating vaginal vault prolapse of patients who accepted passive hysterectomy due to certain diseases, wherein such patients often suffer from pelvic and intestinal adhesions due to surgeries. However, the present invention will not pass through intestine and ureter, enabling shorter surgical learning curve and less complication risk.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A surgery method for inguinal ligament fixation, comprising steps of: at a bladder lithotomy position of a patient, providing routine disinfection for abdominal and perineal skins, and applying a sterile towel; opening a bladder and back-folding a peritoneum; pushing down the bladder for exposing a vaginal wall; fixing a cervix and anterior vaginal wall sling of a suspension mesh on a cervical isthmus with several absorbable or non-absorbable sutures; respectively suturing two sacral ligament and posterior vaginal wall suspension arms of the suspension mesh on a posterior vaginal wall, and fixing the sacral ligament and posterior vaginal wall suspension arms on an inguinal ligament; pulling out two inguinal ligament suspension arms of the suspension mesh along outside portions of peritoneum at two sides of an uterus; opening the peritoneum at a position where a round ligament is attached on the uterus, and suturing the suspension mesh on a myometrium avascular zone under the round ligament; opening the peritoneum below the round ligament; outside the peritoneum and parallel to the round ligament, passing the suspension mesh through anterior superior iliac crest inguinal ligament, fascia and aponeurosis which directly reach an inlet of an inguinal canal, and dragging the suspension mesh until a pre-set length is reached; then opening surface peritoneum of the inguinal ligament and a fascia, and fixing the two inguinal ligament suspension arms on the inguinal ligament, the fascia and the aponeurosis; closing all peritoneal incisions so as to place the suspension mesh outside the peritoneum, and then closing an abdomen.

\* \* \* \* \*